United States Patent [19]

Marcinkowsky et al.

[11] 4,220,803

[45] Sep. 2, 1980

[54] CATALYTIC DEHYDROGENATION OF ETHANOL FOR THE PRODUCTION OF ACETALDEHYDE AND ACETIC ACID

[75] Inventors: Arthur E. Marcinkowsky, Charleston; Joseph P. Henry, S. Charleston, both of W. Va.

[73] Assignee: Union Carbide Corporation, New York, N.Y.

[21] Appl. No.: 919,481

[22] Filed: Jun. 27, 1978

[51] Int. Cl.$^2$ .............. C07C 45/16; C07C 47/06; C07C 51/26; C07C 53/08
[52] U.S. Cl. ................ 562/538; 252/467; 252/476; 560/239; 568/471
[58] Field of Search ............ 562/538; 260/603 C; 252/467, 476

[56] References Cited

U.S. PATENT DOCUMENTS

| | | | |
|---|---|---|---|
| 1,636,952 | 7/1927 | Craver | 260/603 C |
| 1,708,460 | 4/1929 | Zeisberg | 562/538 |
| 1,911,315 | 5/1933 | Haner et al. | 562/538 |
| 1,975,853 | 10/1934 | Lazier | 560/239 |
| 1,977,750 | 10/1934 | Young | 260/603 C |
| 2,160,064 | 5/1939 | Eversale | 562/538 |
| 2,287,803 | 6/1942 | Hull | 560/239 |
| 2,634,295 | 8/1953 | MacLean | 260/603 C |

Primary Examiner—Vivian Garner
Attorney, Agent, or Firm—Bernard Francis Crowe

[57] ABSTRACT

A process for producing acetic acid and acetaldehyde from ethanol which comprises contacting a mixture of ethanol and oxygen with a supported copper oxide catalyst essentially free of barium, the mole ratio of oxygen to ethanol being from about 0.1 to about 0.5.

6 Claims, No Drawings

CATALYTIC DEHYDROGENATION OF ETHANOL FOR THE PRODUCTION OF ACETALDEHYDE AND ACETIC ACID

BACKGROUND OF THE INVENTION

This invention relates to the vapor-phase oxidative dehydrogenation of ethanol to produce acetic acid and acetaldehyde.

The catalytic dehydrogenation of ethanol to produce acetaldehyde is well-known in the art. U.S. Pat. No. 1,977,750 to Young, for example, describes a process wherein ethanol is dehydrogenated over a copper-chromium supported catalyst at a temperature of about 225°–350° C. to form acetaldehyde. Frequently, dehydrogenation of the alcohol is carried out in the presence of air or oxygen which reacts exothermically with the hydrogen generated from the alcohol during the catalytic dehydrogenation reaction. Thus, U.S. Pat. No. 2,634,295 to MacLean, and U.S. Pat No. 3,106,581 to Neely suggest mixing oxygen with alcohol to provide heat to the endothermic dehydrogenation reaction and thereby help maintain the necessary reaction temperature. In addition the presence of oxygen is said to enhance catalyst activity by burning off any carbon deposits on the catalyst surface.

The majority of known processes for preparing acetaldehyde from ethanol are generally incapable of producing acetic acid as a co-product except by a sequential operation wherein the acetaldehyde formed by dehydrogenation is further oxidized to acetic acid in a separate reactor. This represents a significant limitation on the efficiency of acetic acid production. On the other hand, those ethanol dehydrogenation processes which are known to produce acetic acid and acetaldehyde directly from ethanol are generally either characterized by very low selectivities to acetic acid or are operated under conditions which are impractical from the standpoint of a large-scale industrial process. For example, U.S. Pat. No. 1,636,952 to Craver describes a process wherein a mixture of air and ethanol in a ratio of 14:1 (air:ethanol) is passed over a vanadium oxide catalyst resulting in the production of about 10 parts of acetic acid and 70 parts of acetaldehyde per 100 parts of ethanol. Although the reaction produces both acetic acid and acetaldehyde at relatively high efficiencies, it does so using an extremely high oxygen to ethanol mole ratio (about 4:1), the feed being diluted to a point where the energy requirement for pumping the resulting large volume of feed gas through the catalytic reactor seriously affects the over-all process economics.

U.S. Pat. No. 1,911,315 describes a process for producing acetic acid and acetaldehyde wherein air is saturated with ethanol, and the mixture along with water vapor is contacted with a copper oxide catalyst to form the desired products. The drawback of this process, in common with the above-described process of Craver, is the inefficiency associated with pumping a diluted gas phase mixture containing oxygen, ethanol and water vapor through a catalytic reactor. In addition, the energy requirement for vaporization would preclude such operation for a commercial process. Consequently, there remains a need for a vapor-phase oxidative dehydrogenation process capable of operating with a highly concentrated ethanol feed to form acetic acid and acetaldehyde at a relatively high product selectivity of at least 85%.

SUMMARY OF THE INVENTION

The process of the invention comprises contacting a supported copper oxide catalyst which is essentially free of barium, with a mixture of ethanol and oxygen, the mole ratio of oxygen to ethanol varying from about 0.1 to about 0.5. A catalyst mixture of copper and chromium is preferred for purposes of enhancing catalyst life. The primary products of the reaction are acetic acid and acetaldehyde.

It has been surprisingly found that the elimination of barium from an ethanol dehydrogenation catalyst mixture which ordinarily contains the oxides of copper, chromium and barium, such as disclosed in the aforementioned U.S. Pat. No. 2,634,295 to MacLean, provides a catalyst capable of producing acetic acid as well as acetaldehyde at relatively high selectivities directly from an ethanol and oxygen gaseous mixture. Acetic acid and acetaldehyde may be produced at a reaction selectivity of at least 85%, with a yield of acetic acid of at least 5%, when the oxygen to ethanol mole ratio is maintained within the range of about 0.1 to about 0.4. The ratio of 0.5 moles of oxygen per mole of ethanol is a critical upper limit. The presence of oxygen above this limit adversely affects the activity of the copper-chromium catalyst and severely inhibits the formation of acetic acid.

The term "barium" as used throughout the specification and claims encompasses elemental barium as well as other forms of barium such as the oxide.

The reaction "selectivity" to acetic acid and acetaldehyde, as used throughout the specification and claims, is defined as the moles of acetic acid and acetaldehyde produced per mole of ethanol reacted, multiplied by 100.

The term "yield" as used herein with regard to a particular product is defined as the moles of such product per mole of ethanol in the feed mixture, multiplied by 100.

DETAILED DESCRIPTION OF THE INVENTION

The catalyst of the invention is copper oxide supported on an inert porous carrier. The copper is preferably used in a mixture with chromium; the weight ratio of copper to chromium being within the range of about 99:1 to 25:75. A copper:chromium weight ratio of 98:2 is particularly desirable in terms of its activity and catalyst life.

Copper and chromium are deposited on the inert carrier in the oxide form. During reaction, copper oxide may be reduced, in situ, to metallic copper at relatively low oxygen to ethanol mole ratios; chromium is believed to remain in oxide form under all normal operating conditions. The catalyst of the invention is therefore intended to include copper in the oxide form in which it is provided to the reaction, as well as elemental copper which may be formed during the course of the dehydrogenation reaction.

For most effective operation, the amount of catalyst on the support should range from about 2 to 20 weight percent, based upon the combined weight of the metal catalyst and the support material. Preferably, the amount of catalyst is about 10 weight percent.

Alpha alumina is a particularly preferred catalyst carrier. Other carriers which are inert to the dehydrogenation reaction, such as, carbon, silicon carbide and magnesia, may also be used in accordance with the invention, albeit less preferred.

The process of the invention is preferably carried out with the supported catalyst in a fluidized state. The minimum fluidization velocity for the supported copper catalyst is about 0.05 ft/sec. as calculated according to the procedures outlined in "Fluidization" by Leva, McGraw Hill Book Company, Inc. (1959). The maximum fluidization velocity is about 3.50 ft/sec. High linear gas velocities (short contact times) are generally preferred to enhance the reaction productivity. A uniform gas distribution entering the fluid bed reactor is essential to maintain a desired fluidized regime. Fluidization technology applied to catalytic reactors of the gas/solid class discussed here is well-known.

The temperature of the reactor bed is generally maintained within the range of 250°–400° C., and preferably between 285°–325° C. Higher reaction temperatures favor the conversion of ethanol to product both in the presence and absence of oxygen; and dehydrogenation of ethanol to acetaldehyde being highly endothermic and equilibrium controlled. However, the reaction temperatures at which very high conversions can be realized are not normally employed because of the significant increase in undesired side reactions, leading to by-products such as ketones and esters.

DESCRIPTION OF THE TEST REACTOR

The fluidized-bed reactor used in the studies consisted of two sections: a reaction zone consisting of a 1.61" I.D., 3/16" thick stainless steel pipe, 20 inches in length, and a disengaging zone consisting of about a 3" I.D. pipe, 14" in length. The disengaging zone, located above the reaction zone, serves to decrease the linear gas velocity so that most of the entrained catalyst particles will fall back into the reaction zone. The finer particles which are not disengaged from the vapor stream are removed by stainless steel filters located in the upper part of the disengaging zone. An electrically heated tube furnace, 16" in height, was used to jacket the pipe comprising the reaction zone.

Vaporized ethanol feed was pumped into the reactor through a stainless steel frit (or diffuser plate) located 1" above the bottom of the reactor. At the beginning of the experiment the catalyst was added through a separate entrance port at the top of the reactor and at the end of the experiment removed through a catalyst drain located above the stainless steel frit. An inner thermocouple well was positioned in the center of the tube to allow temperature measurement over the entire length of the reactor. The reactor temperature measurements recorded in the examples were taken at a point 11" above the frit.

DESCRIPTION OF THE TEST PROCEDURE

The test reactor which was used in the Examples shown in the Table was operated as follows: Ethanol feed (technical grade) containing 8.29 wt. % water was stored in a graduated reservoir and pumped to a preheater by a dual head pump where it was vaporized and preheated to near reactor temperature conditions. The preheater consisted of an electrically heated 11 ft. coil of SS tubing. The preheater temperature generally remained 10°–15° C. below the temperature of the reactor. A check valve in the feed line prevented the backward flow of vaporized feed. Feed was pumped through the fluidized-bed reactor at rates of 0.3 to 4.2 LHSV (liquid hourly space velocity, defined as liters of ethanol fed at 25° C. per liter of settled catalyst bed per hour). Each experiment lasted from 2–8 hours. Oxygen was introduced into the reactor at a point immediately prior to the preheater. The oxygen flow rate was monitored via gas rotometers.

Gaseous product was removed overhead through a system of filters which removed entrained catalyst particles, thereby delivering a pure gaseous effluent to a water-cooled condenser. A filter blow-back arrangement at the head of the reactor prevented filter clogging. The uncondensed gas which passed through the water condenser was led through a condensation train consisting of wet ice and dry ice/acetone in series so that all low boiling product was recovered. The liquid product was composited, weighed for material balance purposes, and analyzed by standard gas chromatographic techniques.

PREPARATION OF CATALYSTS

The catalysts cited in the Table were all prepared in accordance with the procedure described below: An alpha-alumina catalyst support manufactured by Carborundum Corporation and having the following physical characteristics was used as the carrier: pore volume—0.34 cc/g; surface area—1.28 $m^2/g$; and average particle diameter, harmonic mean, 107 microns.

The desired quantities of copper and chromium acetate, depending upon the desired catalyst composition, are dissolved in water or other suitable solvent at ambient temperature to form the catalyst impregnating solution. For example, for a desired copper-chromium composition having a 96:4 weight ratio, 302 grams of copper acetate and 19 grams of chromium acetate are used. The two salts are dissolved in concentrated $NH_4OH$ to bring the acetate salts into solution. The catalyst support is then impregnated by slowly adding the solution to the support while the latter is being vigorously agitated so as to insure a uniform liquid distribution. If desired, the support may be evacuated prior to impregnation to eliminate possible blockage of the solution by trapped gas. The catalyst solution is generally added at the rate of 300 cc per 1000 grams of support per half hour. The volume of catalyst solution added to the support is preferably just sufficient to completely fill its pore volume.

When using a salt of only moderate solubility, multiple impregnations may be necessary to provide the desired catalyst concentration. Multiple impregnations may also be advantageous to provide a more uniformly dispersed catalyst.

Catalyst impregnation is carried out at room temperature or at elevated temperature. For catalysts impregnated at room temperature, the supports are evacuated prior to addition of the catalyst solution. If for purposes of enhancing solubility, impregnation is carried out at elevated temperatures, the evacuation step is generally omitted. In such case, the equilibration time is lengthened to allow complete solution penetration into the support.

The drying of the impregnated support and the attendant salt decomposition completes the preparation of the supported catalyst. The essential requirement in drying is that the solvent be removed from the support as quickly as possible. Rapid removal of the solvent substantially prevents the salts from migrating during the drying, and produces a catalyst having a surface area which is generally larger than the original surface area of the support.

For the catalysts shown in the Table, the drying-decomposition step was carried out in a quartz tube similar in shape and size to that of the previously described fluidized-bed reactor except that the top of the quartz tube was open and did not contain any filters at the upper end thereof. A heavy-duty heater which surrounded the quartz tube was used to provide the main source of heat. A smaller furnace, which acted as a preheater for the incoming gases, surrounded the part of the tube below the frit which was packed with stainless steel packing; the frit being located at the base of the tube to provide uniform distribution of the gas.

The empty quartz tube was heated to a temperature of from about 300° to 500° C. and maintained at that temperature by using a gas purge, such as air, passing up through the sintered frit. Small samples, 5–10 grams, of impregnated support were then intermittently added through the top of the open tube. Only small amounts of catalyst were added at the start of the heating step because of the relatively low heat capacity of the empty tube. As the catalyst bed is build up, the heat capacity of the system is correspondingly increased and larger sized additions (20–100 g of wet catalyst) may then be added without causing severe temperature fluctuations. The complete addition of the wet support to the hot reactor generally required about one hour. Calcination was then continued for an additional 1–2 hours.

The 96:4 catalyst shown in Examples 6–11 of the Table was prepared by a multiple-impregnation procedure as follows:

302 g of cupric acetate and 19 grams of chromium acetate were dissolved in concentrated $NH_4OH$ to give a final volume of 680 ml. ½ of the resulting solution was then added to 1000 g of corundum support in an evacuated flask, and the impregnated support rapidly dried at about 400° C. After most of the volatiles were thus removed, the acetate salts decomposed and left the metal oxides as residue. The temperature was then raised to about 500° C. and the supported catalyst calcined for an additional 2 hours. The system was then cooled and the procedure repeated once again. The final catalyst contained 10 percent metals based on the weight of support; the metals comprising 96 percent copper and 4 percent chromium.

The data shown in the Table illustrates the effect of temperature and the $O_2$/ethanol mole ratio on reaction selectivity and yield. Those Examples wherein the $O_2$/ethanol mole ratio is 0.5 seem to indicate a general decline in acetic acid yield relative to lower mole ratios. The effect of the $O_2$/ethanol mole ratios is best compared at a single catalyst composition. In Examples 6, 7 and 8 the mole ratio was raised from 0.25 to 0.5 while the selectivity declined from 93 to 88%, respectively, and the acetic acid yield declined from 12.4% to 0.55%. Similar results may be observed for the 90:10 (Examples 12, 13 and 14) and 72:25 (Examples 15, 16 and 17) catalyst compositions.

TABLE

OXIDATIVE-DEHYDROGENATION OF ETHANOL FOR THE CO-PRODUCTION OF ACETALDEHYDE AND ACETIC ACID

| Examples | Acetic Acid & Acetaldehyde Selectivity (%) | Catalyst Composition (Cu:Cr) | Temp. I °C. | Mole Ratio Oxygen Ethanol | Contact Time(sec) | Yield (%) Acetaldehyde | Yield (%) Acetic Acid |
|---|---|---|---|---|---|---|---|
| 1 | 96 | 98:2 | 300 | No $O_2$[a] | 6.4 | 51.3 | 3.08 |
| 2 | 90 | 98:2 | 310 | 0.17 | 3.8 | 53.6 | 7.7 |
| 3 | 83 | 98:2 | 325 | 0.34 | 2.8 | 49.3 | 12.8 |
| 4 | 90 | 98:2 | 310 | 0.24 | 3.17 | 50.9 | 12.3 |
| 5 | 93 | 100:0 | 315 | 0.25 | 2.4 | 58.2 | 11 |
| 6 | 93 | 96:4 | 285 | 0.25 | 2.4 | 41.0 | 12.4 |
| 7 | 90 | 96:4 | 285 | 0.33 | 2.0 | 22.1 | 8.3 |
| 8 | 88 | 96:4 | 280 | 0.50 | 1.6 | 23 | 0.55 |
| 9 | 92.5 | 96:4 | 331 | 0.25 | 2.4 | 57 | 8.8 |
| 10 | 85 | 96:4 | 340 | 0.33 | 2.0 | 52 | 10 |
| 11 | 81 | 96:4 | 360 | 0.50 | 1.6 | 47 | 10.8 |
| 12 | 90.4 | 90:10 | 285 | 0.25 | 2.4 | 43.8 | 13.6 |
| 13 | 76 | 90:10 | 280 | 0.33 | 2.0 | 24.9 | 1.9 |
| 14 | 55 | 90:10 | 280 | 0.50 | 1.6 | 22.8 | 0.9 |
| 15 | 95 | 75:25 | 290 | 0.25 | 2.4 | 46 | 12.2 |
| 16 | 97 | 75:25 | 300 | 0.33 | 2.0 | 46 | 16.3 |
| 17 | 64 | 75:25 | 305 | 0.50 | 1.6 | 29.4 | 2.73 |

Note:
All results are based on 350cc of settled catalyst bed and 10 wt. % of catalyst, based on support weight.
[a] No $O_2$ implies a simple dehydrogenation. The acetic acid which is formed represents acetaldehyde which has undergone a redox reaction of interaction with other by-products of the reaction.

What is claimed is:

1. A process for producing acetic acid and acetaldehyde by the vapor phase oxidative dehydrogenation of ethanol which comprises contacting a mixture of ethanol and oxygen with a catalyst consisting essentially of copper oxide and chromium oxide supported on an inert carrier, which catalyst is essentially free of barium, the mole ratio of oxygen to ethanol being from about 0.1 to about 0.5.

2. The process of claim 1 wherein the weight ratio of copper to chromium in the catalyst is from about 99:1 to 25:75.

3. The process of claim 1 wherein the weight ratio of copper to chromium in the catalyst is about 98:2.

4. The process of claim 1 wherein the amount of catalyst on the support is within the range of about 2 to 20 weight percent based on the weight of catalyst and support material.

5. The process of claim 1 wherein the process is carried out at a temperature of from about 285° to about 325° C.

6. The process of claim 1 wherein the catalyst is maintained in a fluidized state.